(12) United States Patent
Miller

(10) Patent No.: US 12,196,945 B2
(45) Date of Patent: *Jan. 14, 2025

(54) OPTICAL IMAGING DEVICE

(71) Applicant: Scott Miller, Arlington, VA (US)

(72) Inventor: Scott Miller, Arlington, VA (US)

(*) Notice: Subject to any disclaimer, the term of this patent is extended or adjusted under 35 U.S.C. 154(b) by 0 days.

This patent is subject to a terminal disclaimer.

(21) Appl. No.: 18/377,052

(22) Filed: Oct. 5, 2023

(65) Prior Publication Data

US 2024/0241363 A1    Jul. 18, 2024

Related U.S. Application Data

(63) Continuation of application No. 17/870,896, filed on Jul. 22, 2022, now Pat. No. 11,782,257, which is a
(Continued)

(51) Int. Cl.
*G02B 23/24* (2006.01)
*A61B 1/00* (2006.01)
(Continued)

(52) U.S. Cl.
CPC ...... *G02B 23/2423* (2013.01); *A61B 1/00096* (2013.01); *A61B 1/00101* (2013.01);
(Continued)

(58) Field of Classification Search
CPC ........... G02B 23/2423; G02B 23/2349; G02B 23/24; G02B 23/26; G02B 6/262; G02B 6/0008
See application file for complete search history.

(56) References Cited

U.S. PATENT DOCUMENTS 3,774,614 A    11/1973    Cook
3,858,577 A    1/1975    Bass et al.
(Continued)

FOREIGN PATENT DOCUMENTS

CN    1692872 A    11/2011
DE    3532609 A    3/1987
(Continued)

OTHER PUBLICATIONS

European Examination Report for EP Appl. No. 15843356.5 dated May 20, 2019, 7 pages.
(Continued)

*Primary Examiner* — Tina M Wong
(74) *Attorney, Agent, or Firm* — Farber LLC

(57) ABSTRACT

Systems and methods are providing for endoscopically visualizing tissue within a patient. In one aspect, an endoscope comprises an elongate shaft having a distal end and a proximal end and a visualization section at the distal end of the shaft. The visualization section includes a proximal surface and an outer surface spaced apart from the proximal surface. At least one of the proximal surface or the outer surface of the visualization section has an average surface roughness less than about 50 nanometers RMS. The endoscope allows improved remote visualization while not interfering with the autofocus feature of a video capture system and not causing increased light reflectance and glare due to improved surface finish.

19 Claims, 2 Drawing Sheets

Related U.S. Application Data continuation of application No. 17/206,119, filed on Mar. 19, 2021, now Pat. No. 11,428,922, which is a continuation of application No. 16/828,134, filed on Mar. 24, 2020, now Pat. No. 10,989,912, which is a continuation of application No. 16/161,312, filed on Oct. 16, 2018, now Pat. No. 10,642,020, which is a continuation of application No. 15/653,437, filed on Jul. 18, 2017, now Pat. No. 10,101,574, which is a continuation of application No. 15/259,452, filed on Sep. 8, 2016, now Pat. No. 9,709,795, which is a continuation of application No. 14/494,090, filed on Sep. 23, 2014, now Pat. No. 9,459,442.

(51) Int. Cl.
 *F21V 8/00* (2006.01)
 *G02B 6/26* (2006.01)
 *G02B 6/32* (2006.01)
 *G02B 23/26* (2006.01)

(52) U.S. Cl.
 CPC ........ *A61B 1/00137* (2013.01); *G02B 6/0008* (2013.01); *G02B 23/2469* (2013.01); *G02B 23/26* (2013.01); *G02B 6/262* (2013.01); *G02B 6/322* (2013.01)

(56) References Cited

U.S. PATENT DOCUMENTS

| | | |
|---|---|---|
| 4,090,501 A | 5/1978 | Chaitin |
| 4,201,199 A | 5/1980 | Smith |
| 4,207,872 A | 6/1980 | Meiri et al. |
| 4,340,811 A | 7/1982 | Yamashita et al. |
| 4,681,093 A | 7/1987 | Ono et al. |
| 4,696,544 A | 9/1987 | Costella |
| 4,744,620 A | 5/1988 | Ueno et al. |
| 4,779,611 A | 10/1988 | Grooters et al. |
| 4,805,598 A | 2/1989 | Ueda |
| 4,878,725 A | 11/1989 | Hessel et al. |
| 4,881,810 A | 11/1989 | Hasegawa |
| 4,888,243 A | 12/1989 | Jonas et al. |
| 4,967,732 A | 11/1990 | Inoue |
| 5,040,715 A | 8/1991 | Green et al. |
| 5,050,585 A | 9/1991 | Takahashi |
| 5,080,660 A | 1/1992 | Buelna |
| 5,104,025 A | 4/1992 | Main et al. |
| 5,137,198 A | 8/1992 | Nobis et al. |
| 5,201,900 A | 4/1993 | Nardella |
| 5,205,459 A | 4/1993 | Brinkerhoff et al. |
| 5,237,984 A | 8/1993 | Williams, III et al. |
| 5,271,379 A | 12/1993 | Phan et al. |
| 5,326,013 A | 7/1994 | Green et al. |
| 5,329,935 A | 7/1994 | Takahashi |
| 5,337,734 A | 8/1994 | Saab |
| 5,342,388 A | 8/1994 | Toller |
| 5,413,052 A | 5/1995 | Breezer et al. |
| 5,413,268 A | 5/1995 | Green et al. |
| 5,443,781 A | 8/1995 | Saab |
| 5,448,990 A | 9/1995 | De Faria-Correa |
| 5,460,168 A | 10/1995 | Masubuchi et al. |
| 5,471,036 A | 11/1995 | Sperbeck |
| 5,476,206 A | 12/1995 | Green et al. |
| 5,536,236 A | 7/1996 | Yabe et al. |
| 5,555,129 A | 9/1996 | Konno et al. |
| 5,562,602 A | 10/1996 | Yabe et al. |
| 5,569,157 A | 10/1996 | Nakazawa et al. |
| 5,575,291 A | 11/1996 | Hayakawa et al. |
| 5,605,532 A | 2/1997 | Schermerhorn |
| 5,632,717 A | 5/1997 | Yoon |
| 5,657,921 A | 8/1997 | Young et al. |
| 5,662,258 A | 9/1997 | Knodel et al. |
| 5,674,181 A | 10/1997 | Iida |
| 5,707,342 A | 1/1998 | Tanaka |
| 5,725,474 A | 3/1998 | Yasui et al. |
| 5,725,475 A | 3/1998 | Yasui et al. |
| 5,738,629 A | 4/1998 | Moll et al. |
| 5,743,851 A | 4/1998 | Moll et al. |
| 5,771,327 A | 6/1998 | Bar-Or et al. |
| 5,788,628 A | 8/1998 | Matsuno et al. |
| 5,808,813 A | 9/1998 | Lucey et al. |
| 5,840,014 A | 11/1998 | Miyano et al. |
| 5,860,913 A | 1/1999 | Yamaya et al. |
| 5,897,487 A | 4/1999 | Ouchi |
| 5,916,148 A | 6/1999 | Tsuyuki |
| 6,059,719 A | 5/2000 | Yamamoto et al. |
| 6,131,789 A | 10/2000 | Schulze et al. |
| 6,217,509 B1 | 4/2001 | Foley et al. |
| 6,250,532 B1 | 6/2001 | Green et al. |
| 6,277,065 B1 | 8/2001 | Donofrio |
| 6,283,951 B1 | 9/2001 | Flaherty et al. |
| 6,293,907 B1 | 9/2001 | Axon et al. |
| 6,306,081 B1 | 10/2001 | Ishikawa et al. |
| 6,409,725 B1 | 6/2002 | Khandkar et al. |
| 6,416,462 B1 | 7/2002 | Tovey et al. |
| 6,673,091 B1 | 1/2004 | Shaffer et al. |
| 6,699,180 B2 | 3/2004 | Kobayashi |
| 6,712,524 B2 | 3/2004 | Beatty et al. |
| 6,723,350 B2 | 4/2004 | Burrell et al. |
| 6,733,440 B2 | 5/2004 | Ailinger et al. |
| 6,770,069 B1 | 8/2004 | Hobart et al. |
| 6,792,837 B2 | 9/2004 | Battistone |
| 6,855,108 B2 | 2/2005 | Ishibiki et al. |
| 6,866,627 B2 | 3/2005 | Nozue |
| 6,934,093 B2 | 8/2005 | Kislev et al. |
| 6,981,628 B2 | 1/2006 | Wales |
| 6,988,650 B2 | 1/2006 | Schwemberger et al. |
| 7,033,317 B2 | 4/2006 | Pruitt |
| 7,046,439 B2 | 5/2006 | Kaminsky et al. |
| 7,087,012 B2 | 8/2006 | Ishibiki |
| 7,112,195 B2 | 9/2006 | Boll et al. |
| 7,205,339 B2 | 4/2007 | Muratoglu |
| 7,235,592 B2 | 6/2007 | Muratoglu et al. |
| 7,238,153 B2 | 7/2007 | Moriyama |
| 7,245,813 B2 | 7/2007 | Brown et al. |
| 7,464,847 B2 | 12/2008 | Viola et al. |
| 7,537,561 B2 | 5/2009 | Yamaya et al. |
| 7,553,278 B2 | 6/2009 | Kucklick |
| 7,554,743 B2 | 6/2009 | Jiang et al. |
| 7,566,993 B2 | 7/2009 | May |
| 7,621,868 B2 | 11/2009 | Breidenthal et al. |
| 7,819,872 B2 | 10/2010 | Johnson et al. |
| 7,977,255 B1 | 7/2011 | Scheer et al. |
| 8,180,423 B2 | 5/2012 | Mang et al. |
| 8,905,921 B2 | 12/2014 | Titus |
| 8,915,931 B2 | 12/2014 | Boudreaux et al. |
| 9,011,320 B2 | 4/2015 | Weitzner et al. |
| 9,459,442 B2 | 10/2016 | Miller |
| 9,565,991 B2 | 2/2017 | Yamada |
| 9,709,795 B2 | 7/2017 | Miller |
| 10,101,574 B2 | 10/2018 | Miller |
| 10,642,020 B2 * | 5/2020 | Miller ................ A61B 1/00101 |
| 10,989,912 B2 * | 4/2021 | Miller ................ G02B 23/2469 |
| 11,428,922 B2 * | 8/2022 | Miller ................ G02B 6/0008 |
| 11,782,257 B2 * | 10/2023 | Miller ................ G02B 23/2469 359/894 |
| 2002/0035311 A1 | 3/2002 | Ouchi |
| 2002/0065515 A1 | 5/2002 | Falwell et al. |
| 2002/0133148 A1 | 9/2002 | Daniel et al. |
| 2003/0040657 A1 | 2/2003 | Yamaya et al. |
| 2003/0181900 A1 | 9/2003 | Long |
| 2004/0157073 A1 | 8/2004 | Burrell et al. |
| 2004/0249246 A1 | 12/2004 | Campos |
| 2004/0263613 A1 | 12/2004 | Morita |
| 2004/0267092 A1 | 12/2004 | Ishibiki |
| 2005/0043589 A1 | 2/2005 | Pruitt |
| 2005/0080411 A1 | 4/2005 | Ouchi |
| 2005/0131279 A1 | 6/2005 | Boulais et al. |
| 2005/0197530 A1 | 9/2005 | Wallace et al. |
| 2006/0030844 A1 | 2/2006 | Knight et al. |
| 2006/0084839 A1 | 4/2006 | Mourlas et al. |
| 2006/0173241 A1 | 8/2006 | Ouchi et al. |
| 2006/0200176 A1 | 9/2006 | Matsuno et al. |

(56) References Cited

U.S. PATENT DOCUMENTS

| | | |
|---|---|---|
| 2006/0229662 A1 | 10/2006 | Finkielsztein et al. |
| 2006/0270900 A1 | 11/2006 | Chin et al. |
| 2007/0038043 A1 | 2/2007 | Gelikonov et al. |
| 2007/0066869 A1 | 3/2007 | Hoffman |
| 2007/0066870 A1 | 3/2007 | Ohashi et al. |
| 2007/0073108 A1 | 3/2007 | Takahashi |
| 2007/0208219 A1 | 9/2007 | Carter |
| 2007/0239620 A1 | 10/2007 | Schwartz et al. |
| 2007/0260117 A1 | 11/2007 | Zwolinski et al. |
| 2007/0282256 A1 | 12/2007 | Hu et al. |
| 2007/0293888 A1 | 12/2007 | Harren et al. |
| 2008/0021268 A1 | 1/2008 | Shoroji et al. |
| 2008/0021269 A1 | 1/2008 | Tinkham et al. |
| 2008/0033246 A1 | 2/2008 | Matsui et al. |
| 2008/0139885 A1 | 6/2008 | Knapp |
| 2008/0188874 A1 | 8/2008 | Henderson |
| 2008/0262295 A1 | 10/2008 | Kendale et al. |
| 2008/0306335 A1 | 12/2008 | Lau et al. |
| 2009/0048483 A1 | 2/2009 | Yamamoto |
| 2009/0048486 A1 | 2/2009 | Surti |
| 2009/0062790 A1 | 3/2009 | Malchano et al. |
| 2009/0098409 A1 | 4/2009 | Yamada et al. |
| 2009/0143643 A1 | 6/2009 | Weitzner et al. |
| 2009/0156898 A1 | 6/2009 | Ichimura |
| 2009/0254164 A1 | 10/2009 | Johnson et al. |
| 2009/0264154 A1 | 10/2009 | Rofougaran |
| 2009/0315989 A1 | 12/2009 | Adelson |
| 2009/0326328 A1 | 12/2009 | Kucklick |
| 2010/0026940 A1 | 2/2010 | Takegami et al. |
| 2010/0121442 A1 | 5/2010 | Shea et al. |
| 2010/0203454 A1 | 8/2010 | Brongersma et al. |
| 2010/0268027 A1 | 10/2010 | Aono et al. |
| 2010/0286475 A1* | 11/2010 | Robertson .......... A61B 1/00188 600/109 |
| 2011/0124960 A1 | 5/2011 | St. Onge et al. |
| 2011/0152618 A1 | 6/2011 | Surti |
| 2012/0034573 A1 | 2/2012 | Erdmann et al. |
| 2012/0209074 A1 | 8/2012 | Titus |
| 2012/0209090 A1 | 8/2012 | Goodall et al. |
| 2012/0232342 A1 | 9/2012 | Reydel |
| 2013/0040516 A1 | 2/2013 | Pruneri et al. |
| 2013/0046138 A1 | 2/2013 | McLawhorn |
| 2013/0090527 A1 | 4/2013 | Axon |
| 2013/0144287 A1 | 6/2013 | Crowley et al. |
| 2013/0190562 A1 | 7/2013 | Smith et al. |
| 2013/0237998 A1 | 9/2013 | Wallace et al. |
| 2015/0073214 A1 | 3/2015 | Ueda |
| 2016/0051135 A1 | 2/2016 | Greenberg et al. |
| 2016/0270636 A1 | 9/2016 | Iwasaka et al. |
| 2017/0066111 A1 | 3/2017 | Wang |
| 2017/0311789 A1 | 11/2017 | Mulcahey et al. |
| 2020/0100655 A1 | 4/2020 | Morishima et al. |

FOREIGN PATENT DOCUMENTS

| | | |
|---|---|---|
| EP | 1870018 A2 | 12/2007 |
| JP | H0373168 A | 3/1991 |
| JP | 07-178094 | 7/1995 |
| JP | H09238893 A | 9/1997 |
| JP | 05-123288 | 5/1999 |
| JP | 2000300570 A | 10/2000 |
| JP | 3124079 B2 | 1/2001 |
| JP | 2002233491 A | 8/2002 |
| JP | 2003033319 A | 2/2003 |
| JP | 2003339631 A | 12/2003 |
| JP | 2005066139 A | 3/2005 |
| JP | 2006026344 A | 2/2006 |
| JP | 2008-029384 | 2/2008 |
| JP | 2009261830 A | 11/2009 |
| JP | 5854805 | 2/2016 |
| WO | WO 9929362 A1 | 6/1999 |
| WO | WO 2001085319 A1 | 11/2001 |
| WO | WO 2006138409 A2 | 12/2006 |
| WO | WO 2007029230 A2 | 3/2007 |
| WO | WO 2007029814 A1 | 3/2007 |
| WO | WO 2007147060 A2 | 12/2007 |
| WO | WO 2009149042 A2 | 12/2009 |
| WO | WO 2011085319 A1 | 7/2011 |
| WO | WO 2011099329 A1 | 8/2011 |
| WO | WO 2011148172 A2 | 12/2011 |
| WO | WO 2014123563 A1 | 8/2014 |
| WO | WO 2017011535 A1 | 1/2017 |

OTHER PUBLICATIONS

Extended European Search Report for EP Appl. No. 16828548.4 dated Feb. 28, 2019.
Extended European Search Report for EP Appl. No. 16804476.6 dated Dec. 5, 2018.
Extended European Search Report and Written Opinion for EP Appl. No. 16804462-6 dated Dec. 10, 2018.
Extended European Search Report for EP Appl. No. 12747511.9 dated Jan. 3, 2018.
Extended European Search Report for EP Appl. No. 18174913.6 dated Aug. 16, 2019.
International Preliminary Report on Patentability issued in PCT/US2015/051662 dated Apr. 6, 2017.
International Search Report and Written Opinion for PCT Appl. No. PCT/US2019/012448 mailed Apr. 16, 2019.
International Search Report and Written Opinion dated Oct. 26, 2016 for PCT Application No. PCT/US2016/043371, filed Jul. 21, 2016.
International Search Report issued in corresponding International Application No. PCT/US2015/051662 dated Dec. 14, 2015.
International Search Report and Written Opinion dated Sep. 21, 2012 for PCT Appl. No. PCT/US2012/025404.
Japanese Patent Office, Notification of Reasons for Refusal, JP Appl. No. 2013-554596, Dec. 8, 2015.
Chinese Office Action and Search Report for CN Appl. No. 201280014363, Mar. 23, 2015.
Chinese Office Action for CN Appl. No. 201280014363, Jan. 5, 2016.
Chinese Office Action for CN Appl. No. 201680045602.6 dated Jun. 5, 2019.
First Examination Report for Indian Appl. No. 6566/CHENP/2013 dated Aug. 29, 2019.
Beneq Biocompatible Coatings Webpage.
Cargille Laboratories, Inc. Material Safety Data Sheet_13 Cargille Optical Gel Code 0607, Jun. 3, 2005.
Depth of Field, OPMI Application Tip #2, Informed for Medical Professionals in Neuro, ENT and Spine, 2nd Issue, Oct. 2006, Published by Carl Zeiss Surgical GmbH, Germany.
Jaxton, et al., An Experimental Investigation on the Development of Hydrogels for Optical Applications, Polymer Testing, 2003, 22(4):371-374, English Abstract.
Kopp, et al., Chapter 9, Optical Principles of the Endoscope, Hysteroscopy: Visual Perspectives of Uterine Anatomy, Physiology & Pathology, 3rd Edition, Lippincott Williams & Wilkins, 2007, 19 pages.
Maquet Training Manual, Vasoview 6 Endoscopic Vessel Harvesting System, Cardiovascular, Copyright Maquet Cardiovascular LLC, Oct. 2008.
Oil Immersion, From Wikipedia, http://en.wikipedia.org/wiki/Oil.sub.--immerson, Printed Sep. 7, 2010.
Olympus Colonoscopes Outpatient Doctor Surgery Center, http://outpatientsurgicare.com/index.PHP?Facilities:Technologies:Olympus.sub.--Colonoscopes&print, Printed Oct. 26, 2010.
Olympus Disposal Distal Attachment Product Data Sheet.
Olympus Evis Exera Colonovideoscope/Sigmoidovideoscope, Olympus CF Type Q1601JUS, Today's Most Versatile Choice for Colonoscopy, Product Data Sheet.
Olympus Technologies Evis Exera II, Learn About Wide—Angle, http://www.olympusamerica.com/msg.sub.--section/ msg.sub.--endoscopy.sub.--technology.asp, Copyright 2010 Olympus America Inc.

(56) References Cited

OTHER PUBLICATIONS

Olympus Technologies Evis Exera II, Learn About Close Focus, http://www.olympusamerica.com/msg.sub.--section/ msg.sub.--endoscopy.sub.--technology.asp, Copyright 2010 Olympus America Inc.

Olympus NA-11J-KB Product Data Sheet.

Optical Gels for Fiber-Optic Connectors and Splices—A Tutorial, Nye Optical Products, 6 pages.

Paxton, et al., An Experimental Investigation on the Development of Hydrogels for Optical Applications, Polymer Testing, 2003, 22(4):371-374, English Abstract.

Sigma-Aldrich Poly(2-hydroxyethyl methacrylate) Product Data Sheet, http://www.sigmaaldrich.com/catalog/Product Detail, Copyright 2010 Sigma-Aldrich Co.

Sigma-Aldrich Poly(ethylene glycol) Product Data Sheet, http://www.sigmaaldrich.com/catalog/Product Detail, Copyright 2010 Sigma-Aldrich Co.

Sigma-Aldrich Poly(vinyl alcohol) Product Data Sheet, http://www.sigmaaldrich.com/catalog/Product Detail, Copyright 2010 Sigma-Aldrich Co.

Sigma-Aldrich Methacrylic acid Product Data Sheet, http://www.sigmaaldrich.com/catalog/Product Detail, Printed Sep. 3, 2010.

SmartGel Nye Nyogel OCK-451LPH Product Data Sheet, Nye Optical Products.

Smeds, et al., Photocrosslinkable Polysaccharides for in situ Hydrogel Formation, Journal of Biomedical Materials Research, 2001, 54:115-121.

Stadler, Transparent conducting oxides—An up-to-date overview, Materials 5.4:661-683, 2012.

The Basics of Silicon Chemistry, Basic Silicon Production and Siloxane Polymerization, http://www.dowcorning.com/ content/sitech/sitechbasics/siloxane.sub.--poly- merization.asp, Copyright 2000-2010 Dow Corning Corporation.

Uw Eye Research Institute, Newsletter, Point of View, Summer 2009, http://vision.wisc.edu/news.sub.--sum09.html, Printed Feb. 5, 2010.

Vinyl Sustainability Forum 2014, Title: Benefits of PVC, Date retrieved: Mar. 7, 2014 from website: http://www.pvc.org/ en/p/benefits-of-pvc, pp. 1-4.

Zeng, et al., An Endoscope Utilizing Tunable-Focus Microlenses Actuated through Infrared Light, Solid-State Sensors, Actuators and Microsystems Conference, 2009, Transducers 2009, International, Issue 21-25, pp. 1214-1217, Abstract Only.

Zeng, et al., Tunable Liquid Microlens Actuated by Infrared Light-Responsive Hydrogel, Applied Physics Letters, 2008, 93:151101-1-151101-3.

US Patent and Trademark Office; Office Action issued in U.S. Appl. No. 16/828,134, dated Oct. 30, 2020.

Chinese Office Action for Chinese Patent Application No. 201680054885.0 dated Jun. 3, 2020.

Chinese Office Action for CN Appl. No. 20168004557.9 dated Mar. 24, 2020.

* cited by examiner

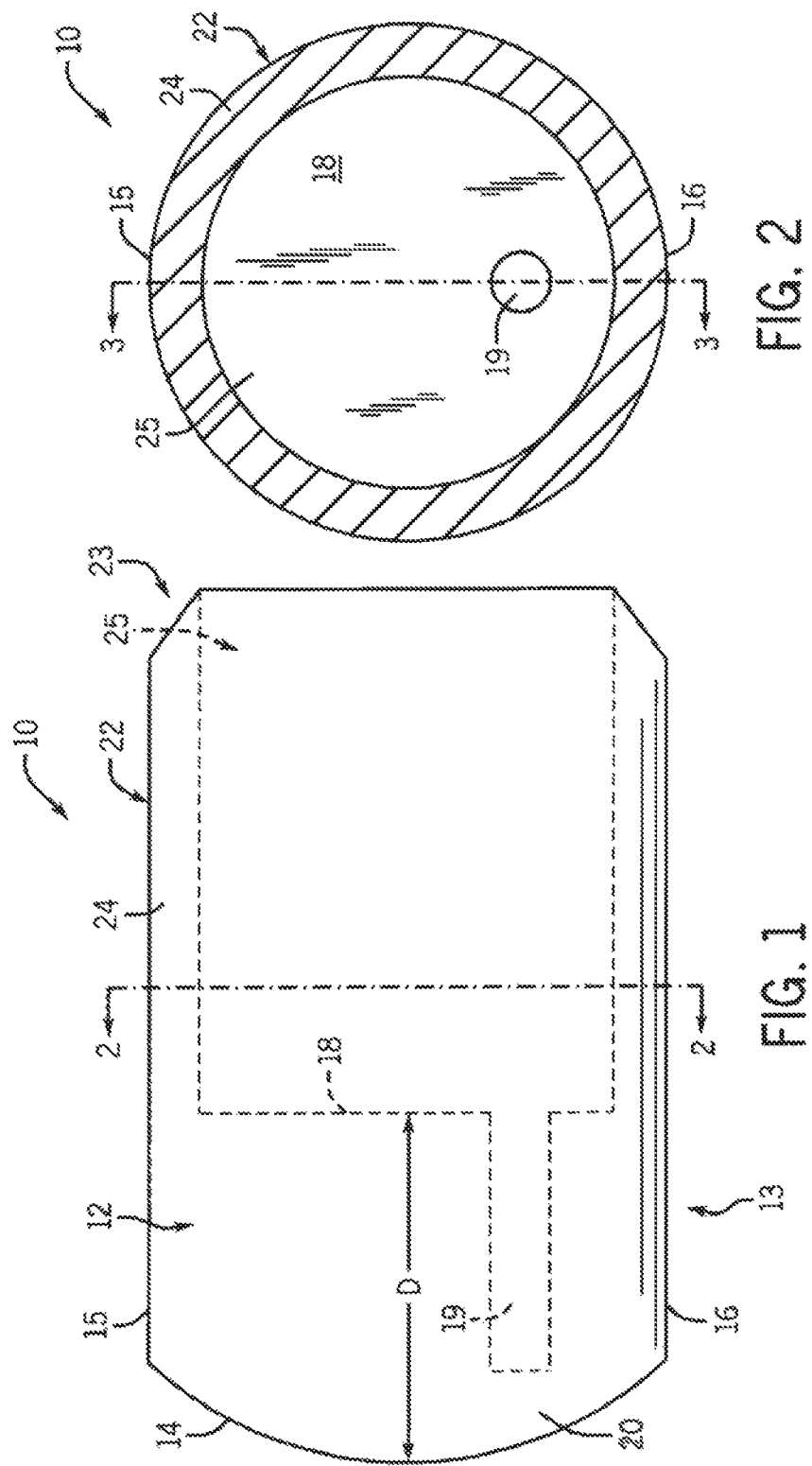

OPTICAL IMAGING DEVICE

CROSS-REFERENCE TO RELATED APPLICATIONS

This application is a continuation of U.S. patent application Ser. No. 17/870,896, filed Jul. 22, 2022 which is a continuation of U.S. patent application Ser. No. 17/206,119, filed Mar. 19, 2021, which is a continuation of U.S. patent application Ser. No. 16/828,134, filed Mar. 24, 2020 (now U.S. Pat. No. 10,989,912), which is a continuation of U.S. patent application Ser. No. 16/161,312, filed Oct. 16, 2018 (now U.S. Pat. No. 10,642,020), which is a continuation of U.S. patent application Ser. No. 15/653,437, filed Jul. 18, 2017 (now U.S. Pat. No. 10,101,574), which is a continuation of U.S. patent application Ser. No. 15/259,452, filed Sep. 8, 2016 (now U.S. Pat. No. 9,709,795), which is a continuation of U.S. patent application Ser. No. 14/494,090, filed Sep. 23, 2014 (now U.S. Pat. No. 9,459,442) the entire disclosures of which are incorporated herein by reference for all purposes.

FIELD

Systems and methods are provided for improved optical imaging of target areas by an optical imaging visualization device, such as an endoscope, laparoscope, arthroscope, ophthalmoscope, borescope, or other remote imaging visualization technology.

BACKGROUND

Remote optical visualization devices such as endoscopes and other optical imaging visualization devices illuminate surfaces and other objects a distance from the user of the visualization device, allowing a user to perform a diagnosis or procedure using images and signals generated and transmitted a distance from the observed object. This can include, for example, viewing tissue inside a body cavity or a lumen, inspecting a hydraulic line in an aircraft, inspecting an oil pipeline for leaks, or inspecting a sewer line for leaks and/or blockages. Remote optical visualization devices transmit these images to the viewer in a variety of ways, including, among others, through the use of (i) relay lenses between the objective lens at the distal end of the scope and an eyepiece, (ii) fiber optics, and (iii) charge coupled devices (CCD) and complementary metal oxide semiconductor (CMOS) sensors. Frequently, a video capture system is connected to the optical visualization device to display a video image on a display monitor that can be viewed by a user during use of the optical visualization device, including the ability to adjust the focus of the display through manual adjustments or autofocus capability in a video processor system used with the optical imaging device. To achieve video capture with a video processor system, an objective lens of an optical visualization device focuses light reflected from a target being observed on an image sensor. The image sensor outputs signals based on the detected reflected light. The signals from the image sensor are output to a signal processor, which typically includes imaging software that controls an autofocus feature connected to the objective lens to adjust the in-focus object plane position. A control signal generated by the signal processor activates an autofocus operation to automatically bring the target being observed into focus.

Optical couplers positioned over the objective image capturing element of an optical visualization device allow improved remote observation in areas of the body where visibility has been obstructed by blood, stomach content, bowel content, or other opaque fluids and/or solid particulate matter. Optical couplers also allow improved remote observation in non-medical applications where visibility has been obstructed by fluids and/or solid particulate matter. However, imperfections on the surface of the optical coupler may inhibit the visualization of the optical visualization device, including confusing the signal processor of an optical visualization device using a video capture system, causing the autofocus feature to focus the objective lens on a surface of the optical coupler, rather than on the intended target to be observed. Further, when an optical coupler is used with visualization systems that do not use image capture software, visualization may be hindered when the light from the visualization system passes through imperfections on the distal surface of the optical coupler resulting in increased light reflection and increased glare due to these imperfections. This may occur when light proceeds through the optical coupler and when light returns back through the optical coupler to the scope camera.

It would be advantageous to provide an endoscope that allows improved remote visualization while not interfering with the autofocus feature of a video capture system and not causing increased light reflectance and glare due to improved surface finish.

SUMMARY

Endoscopes are provided with one or more distal surfaces having a defined degree of roughness. In embodiments, a surface of the endoscope has a Root Mean Square (RMS) Roughness below about 20 nanometers, in embodiments from about 5 nanometers to about 18 nanometers. In embodiments, the surface roughness of the endoscope surface is below about 0.5 nanometers, in embodiments from about 0.1 nanometers to about 0.4 nanometers. In embodiments, a surface of the endoscope has a Root Mean Square (RMS) Roughness below about 20 nanometers with spatial frequencies between $1 \times 10^{-1}$ mm-1 to $1 \times 10^3$ mm-1, in embodiments Y from about 5 nanometers to about 18 nanometers for a similar spatial frequency range.

The "surface roughness of the endoscope surface is below about 0.5 nanometers" means that one of the center-line mean roughness (Ra), the ten-point height irregularities (Rz), and the maximum height roughness (Rmax) is less than 0.5 nanometers, ±0.05 nanometers. In embodiments, a surface of the endoscope has a center-line mean roughness (Ra) of no more than about 0.5 nanometers, in embodiments, from about 0.1 nanometers to about 0.4 nanometers. In embodiments, a surface of the endoscope has a ten-point height irregularities (Rz) of no more than about 0.5 nanometers, in embodiments, from about 0.1 nanometers to about 0.4 nanometers. In embodiments, a surface of the endoscope has a maximum height roughness (Rmax) of no more than about 0.5 nanometers, in embodiments, from about 0.1 nanometers to about 0.4 nanometers. In embodiments, a surface of the endoscope has an average defect density of no more than about 100 defects per 10 $\mu m^2$, in embodiments from about 10 defects per 10 $\mu m^2$ to about 75 defects per 10 $\mu m^2$. In embodiments, the distal surface of the endoscope has a defined degree of roughness. In embodiments, the surface of the endoscope closest to the objective lens has a defined degree of roughness.

BRIEF DESCRIPTION OF THE DRAWINGS

The above and other aspects, features, and advantages of the present disclosure will become more apparent in light of the following detailed description when taken in conjunction with the accompanying drawings in which:

FIG. 1 is a side view of a first embodiment of an optical coupler;

FIG. 2 is a cross-sectional view of the optical coupler of FIG. 1 taken along line 2-2 of FIG. 1.

Figure 3:
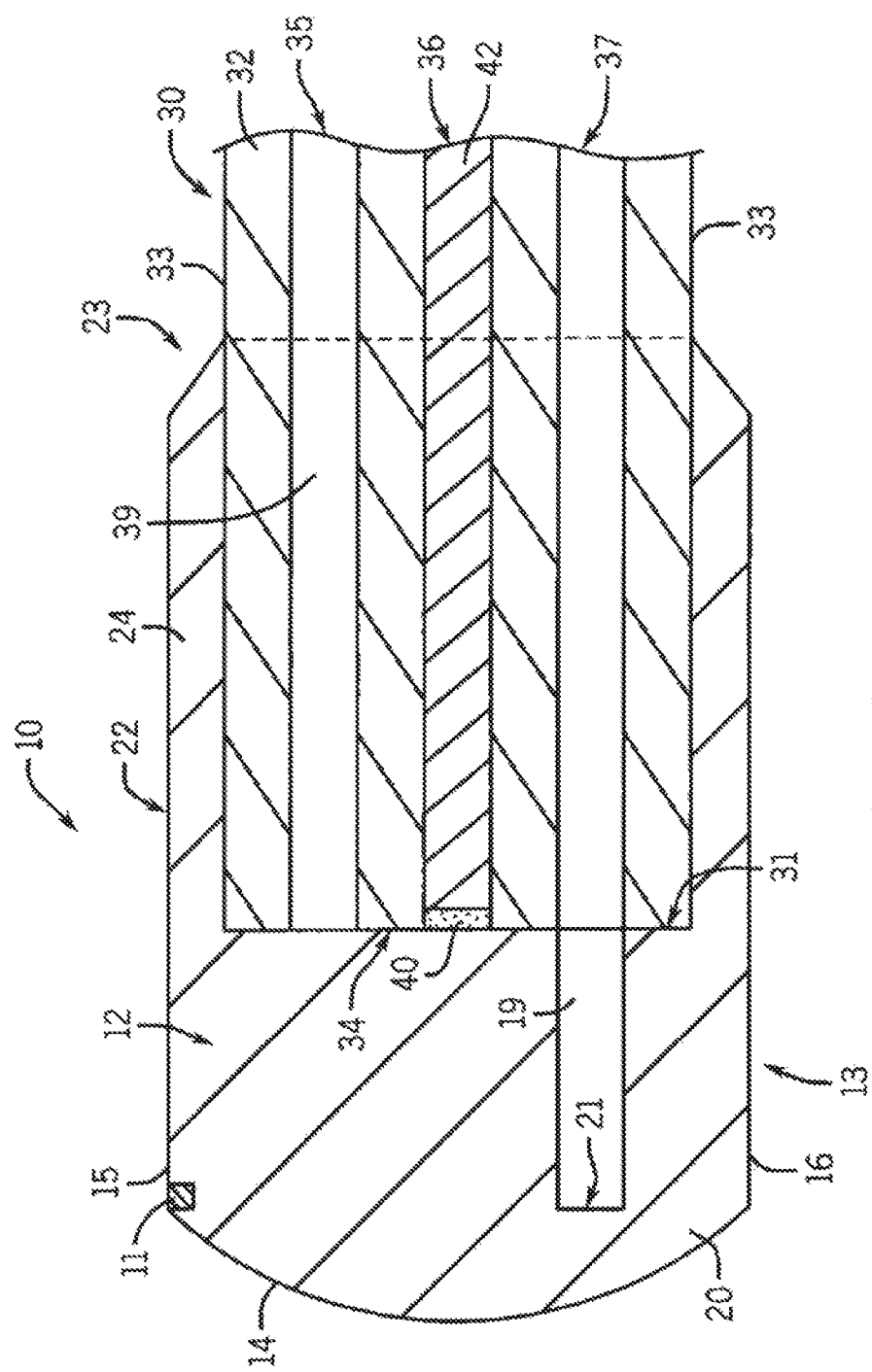
FIG. 3 is a cross-sectional view of the optical coupler of FIGS. 1 and 2 taken along line 3-3 of FIG. 2, the optical coupler being attached to an endoscope.

The figures depict specific embodiments of the present disclosure for purposes of illustration only. One skilled in the art will readily recognize from the following discussion that alternative embodiments of the structures and methods illustrated herein may be employed without departing from the principles of the present disclosure described herein.

DETAILED DESCRIPTION

The present endoscopes provide for improved optical imaging of surfaces covered with opaque fluids, semisolid materials or particulate matter, without interfering with the autofocus feature and other image capture and transmission elements of the optical imaging visualization device and its related system elements. These advantages are provided by ensuring that one or more surface(s) of the endoscope in the optical path has a defined degree of roughness, as described in more detail below.

The devices and methods described herein can be used in various applications. With Natural Orifice Translumenal Endoscopic Surgery (NOTES), the coupler enables procedures to continue when unexpected bleeding or other fluids such as bile or stomach contents obstruct the view. Also, the coupler can create or increase working space by pushing organs out of the field of view. With a laryngoscope in trauma and emergency situations, the coupler would push blood, foreign objects, or food away to increase visibility to allow visualizing of the trachea. When taking biopsies is required, the coupler isolates the intended biopsy target, the tumor or area to be biopsied from surrounding tissue. Close focusing and contact with the tissue with the aid of the coupler can improve reliability by allow multiple biopsies to taken in exact locations defining borders of the tumor, and minimize tumor cells from entering the blood stream or lymph channels. A cautery probe or electrode can be used simultaneously or in conjunction with the biopsy forceps, minimizing bleeding and length of procedure.

The coupler can be used in various endoscopic intra-cardiac procedures such as: (1) myocardial biopsy (for transplant monitoring or tumor sampling); (2) valve repair or reconstruction; (3) patent foramen oval (PFO) closure; (4) ventricle septal defect (VSD) closure; (5) pacing wire placement or removal; (6) stem cell injection; (7) coronary sinus cannulations (8) and maze procedure. In cryoablation, a specialized composite coupler could be made that has warming channels to warm the external surface of the coupler to protect surrounding tissue from freezing. In radiofrequency ablation, insulating and isolating properties of the coupler would concentrate power, protecting surrounding tissue.

The coupler can be used in various vascular procedures. The coupler can be used to guide proper placement of covered stents in dissected aortas, or visualize an intravascular laser. The coupler could be used to inspect the suture line of a large or small vessel anastomosis to evaluate the quality of the suturing and or determine the location of any bleeding.

In certain surgical or trauma situations there is severe arterial bleeding from a wound or vessel. Often the first action taken is to compress a finger or sponge on the area of bleeding. After time passes the finger or sponge is removed. If the bleeding continues either more compression or other actions are taken such as blind clamping, suctioning the blood away and then clamping and suturing, or homeostatic materials are applied. Blood loss can be substantial. An embodiment mounted at the end of a finger shaped wand can be compressed over a bleeding site, both clearing the field of blood and creating a view to locate the point of bleeding. Since the coupler is clear, soft and biocompatible, a suture or staple can be passed though the coupler to repair the bleeding site.

The working channels within the coupler or parallel to the coupler allow surgical instruments, probes, biopsy needles, needles, sutures etc. to be passed to the area being viewed. Since the coupler is flexible, the channels can move within or around the coupler without compromising its function. One enabling property of the coupler is its soft flexible shape that conforms to the tissue or object being viewed. This characteristic reduces damage to delicate tissues or structures.

Another advantage of the coupler is that only the specific area being viewed through the coupler attached to the endoscope requires illumination and therefore, the targeted view requires less light to be supplied by the endoscope lighting system. Because the number of light fibers required for illumination is less, endoscopes can be smaller or less expensive to manufacture. Also, since it is only necessary to illuminate the area of the coupler at its outer boundary, endoscopes of smaller diameter would be required to view a targeted area.

The coupler can be a semi-solid gel, which is transparent and flexible, that attaches to a wide variety of endoscopes. For minimally invasive procedures, the smallest possible scope is used. The optimal shape and size of the coupler can be determined by the field of view of the endoscope, or conversely an endoscope can be chosen that will match the size and shape of the coupler. The shape of the coupler can be manufactured with a preformed shape matched to the contour of the object that will be examined, for example an endoscope coupler could be made in the shape of the blood pool at the apex of the heart. This coupler can be used in conjunction with a 2 mm angioscope maneuvered into the apex of the heart and displace the blood to visualize the inside wall of the ventricle of the beating heart.

The coupler can be attached to the endoscope with a clear adhesive material. The coupler can be attached as a screw on auxiliary lens or filter allowing different couplers with different purposes or functions to be utilized with the same scope. The coupler can be attached and held in place with suction. The coupler can be attached by sewing on with sutures. The coupler can be attached with wire, nylon or other braid material. The coupler can be attached to endoscopes with mesh or pliable membranes. When using a mesh net to attach the coupler to the endoscope, gel strength and viscosity must be high enough to prohibit gel flow through holes in the outer layer of mesh.

A coupler can be compressed in a tube fixed to the end of the scope. A coupler attached to the endoscope can be compressed in a retractable sheath. Embodiments of the coupler can have one, two or more working channels that align with the endoscope's working lumens. Other versions of the coupler allow for additional internal channels or along the edges of the device for use in more complex procedures, such as suturing.

The coupler can be used in any minimally invasive procedure. Biopsies in the body, for example, could be taken under direct view, reducing the need for $CO_2$ inflation. The coupler allows exact placement of needles and medical devices in situations where active bleeding or other bodily fluids impede visibility. The coupler can be held with pressure over an active bleeding site to stop bleeding until the suturing process, stapling, clamping or medical device placement is complete.

Turning now to FIGS. 1-3, an embodiment of an optical coupler 10 is shown. The optical coupler 10 includes a visualization section 12 at a distal end 13 of optical coupler 10. Visualization section 12 has a generally slightly curved, convex outer surface 14 that extends from a first outer side boundary 15 to a second opposite outer side boundary 16 of optical coupler 10, and a proximal surface 18. In other embodiments, the visualization section may be non-curved and other embodiments may be concave. Outer surface 14 may be spaced apart from proximal surface 18 of optical coupler 10 by a length D (see FIG. 1). In some embodiments, a hollow instrument channel 19 extends from proximal surface 18 toward outer surface 14. Instrument channel 19 may not extend all the way through visualization section 12 to the outer surface 14. In such a case, a barrier section 20 of material is provided between a distal end 21 of instrument channel 19 and outer surface 14 of optical coupler 10.

Optical coupler 10 also includes an attachment section 22 connected to and extending away from visualization section 12. Attachment section 22 is at the proximal end 23 of optical coupler 10. In the embodiment shown, attachment section 22 is in the form of a cylindrical wall 24. Proximal surface 18 and cylindrical wall 24 of optical coupler 10 define a cylindrical opening 25 of optical coupler 10 within cylindrical wall 24. In other embodiments, the optical coupler may be attached in other manners, including using a gel or glue.

Referring to FIG. 3, optical coupler 10 can be mounted on an endoscope 30. Endoscope 30 has a distal end 31 that is inserted in cylindrical opening 25 of optical coupler 10. Endoscope 30 has a sheath 32 with an outer surface 33 that snugly engages cylindrical wall 24 of optical coupler 10. An end surface 34 of endoscope 30 sealingly engages proximal surface 18 of optical coupler 10. Endoscope 30 includes a first lumen 35, a second lumen 36 and a third lumen 37 that extend from end surface 34 of endoscope 30 to a proximal end (not shown) of endoscope 30. A light guide 39 positioned in the first lumen 35 transmits light toward a surface area at or beyond outer surface 14 of optical coupler 10. An objective lens 40 is optically connected to a distal end of image carrying fiber 42. Objective lens 40 receives light reflected from the surface area being viewed and image carrying fiber 42 transmits the reflected light to a video capture system (not shown) at a proximal end (not shown) of image carrying fiber 42. Objective lens 40 and image carrying fiber 42 are located in second lumen 36. Third lumen 37 aligns with hollow instrument channel 19 of optical coupler 10 when optical coupler 10 is mounted on endoscope 30. Optical coupler 10 can also include a Light Emitting Diode (LED) 11 near outer surface 14 of the coupler to provide illumination prior to optical coupler 10 contacting any fluids, tissue, or structure. LED 11 may be provided power via a wire (not shown) in endoscope 30 or from an external source. Additional details regarding the construction and alternative embodiments of suitable optical couplers can be found in Published U.S. Patent Application No. US2012/0209074A1, the entire content of which is incorporated herein by this reference.

Outer surface 14 and proximal surface 18 of optical coupler 10 lie within the optical path of objective lens 40. In accordance with the present disclosure, at least one of outer surface 14 or proximal surface 18 of optical coupler 10 is provided with a defined degree of roughness. The degree of roughness is the aggregate of any textural constituent elements present on the lens. The size of the textural constituent element is not particularly limited provided the overall degree of roughness does not interfere with the visualization of the image transmitted by the image capture system associated with the endoscope onto which the optical coupler has been mounted.

In embodiments, the outer surface of the coupler transmits both the light used for illumination and the returning light used for imaging simultaneously. This common-path illumination and imaging lens allows for uniform illumination of an object near or at the focal region of the optical imaging visualization device. However because of this, any surface defects may cause light to be refracted or reflected back toward the camera and cause glare or reduced contrast. Also, even a very smooth transmitting surface will reflect a small percentage of light due to Fresnel reflections; therefore, the figure and location of the lens surface must be controlled such that light emitted from the illumination source will not reflect as such angles as to cause unwanted glare along with the surface finish with a defined degree of roughness.

In embodiments, the length and the width of any given textural constituent element can both be 10 μm or less. In embodiments, the length of the textural constituent element (size of the textural constituent element in the longer direction) is 3 μm or less and the width (size of the textural constituent element in the shorter direction) 500 nm or less. In other embodiments, the length and the width of the textural constituent element are preferably in the range of 3 μm to 50 nm. In embodiments, the depth of the textural constituent element may be 15 nm to 200 nm.

In embodiments where outer surface 14 or proximal surface 18 of optical coupler 10 includes depressions, the depressions have an average diameter less than 100 nanometers, in embodiments, from about 15 to about 50 nanometers. The depressions may have an average depth less than about 100 nanometers, in embodiments from about 4 nanometers to about 50. The depressions may have a density or an average density, meaning the number of depressions per 100 square micrometers of surface or the average number of depressions per 100 square micrometers of surface, of less than about 100 depressions per 100 square micrometers of surface, in embodiments from about 15 to about 50 depressions per 100 square micrometers of surface.

In embodiments, a surface of the optical coupler has a Root Mean Square (RMS) Roughness below about 200 Angstroms; in embodiments, from about 50 Angstroms to about 180 Angstroms. In embodiments, the surface roughness of the optical coupler surface is below about 0.5 nanometers, in embodiments from about 0.1 nanometers to about 0.4 nanometers. The "surface roughness of the optical coupler surface is below about 0.5 nanometers" means that one of the center-line mean roughness (Ra), the ten-point height irregularities (Rz), and the maximum height roughness ($R_{max}$) is less than 0.5 nanometers, ±0.05 nanometers. In embodiments, a surface of the optical coupler has a center-line mean roughness (Ra) of no more than about 0.5 nanometers, in embodiments, from about 0.1 nanometers to about 0.4 nanometers. In embodiments, a surface of the optical coupler has a ten-point height irregularities (Rx) of no more than about 0.5 nanometers, in embodiments, from about 0.1 nanometers to about 0.4 nanometers. In embodiments, a surface of the optical coupler has a maximum height roughness ($R_{max}$) of no more than about 0.5 nanometers, in embodiments, from about 0.1 nanometers to about 0.4 nanometers. In embodiments, a surface of the optical coupler has an average defect density of no more than about 100 defects per 10 µm², in embodiments from about 10 defects per 10 µm² to about 75 defects per 10 µm². In embodiments, outer surface 14 of optical coupler 10 has a defined degree of roughness. In embodiments, proximal surface 18 of optical coupler 10 (i.e., the surface closest to the objective lens of the endoscope) has a defined degree of roughness.

The degree of roughness can be determined by using any technique within the purview of those skilled in the art, such as, for example, a laser surface analyzer or a stylus surface profiler, but it can also be determined, simply by direct observation of the surface and cross section under SEM.

A defined degree of roughness is provided on a surface of the optical coupler using techniques within the purview of those skilled in the art. The specific method chosen will depend on a number of factors including the material from which the optical coupler is made.

Optical coupler 10 can be formed from a variety of materials exhibiting transparency or translucency and biocompatibility in medical applications. In embodiments, an optical coupler for non-medical applications can be formed from a variety of materials exhibiting transparency or translucency.

In embodiments, a rigid material, e.g., a resin material such as cycloolefin polymer or polycarbonate, is used to form the optical coupler. When rigid materials are used, they are typically molded and then one or more surface is polished to impart a defined degree of roughness. Polishing techniques are within the purview of those skilled in the art and include, for example, chemical-mechanical polishing, mechanical polishing, CMP processes, reactive ion etching (e.g., with a substantially chemically etching component), physical etching, and wet etching.

In embodiments, a flexible material is used to form the optical coupler. Flexible materials are typically difficult to polish. Accordingly, where flexible materials are used, a defined degree of roughness is provided on the surface of a mold and imparted to the optical coupler when it is molded.

In embodiments, the mold is prepared by any technique within the purview of those skilled in the art, such as for example, the use of a series of micropolish compounds to prepare and refine the finish of the mold to the point where the mold can produce an optical coupler with the desired surface finish on the optical coupler, and, alternatively, creating the mold using single-point diamond turning to cut the surface of the mold with a level of refined surface that the mold produces an optical coupler with the desired surface finish on the optical coupler.

In embodiments, optical coupler 10 is molded from a material selected from glass, silicone gels, silicone elastomers, epoxies, polyurethanes, polycarbonates, acrylics, other elastic materials, and mixtures thereof. The silicone gels can be lightly cross-linked polysiloxane (e.g., polydimethylsiloxane) fluids, where the cross-link is introduced through a multifunctional silane. The silicone elastomers can be cross-linked fluids whose three-dimensional structure is much more intricate than a gel as there is very little free fluid in the matrix. In other embodiments, optical coupler 10 is made from a material selected from hydrogels, such as polyvinyl alcohol, poly(hydroxyethyl methacrylate), polyethylene glycol, poly(methacrylic acid), and mixtures thereof. The material for optical coupler 10 may also be selected from albumin based gels, mineral oil based gels, polyisoprene, or polybutadiene. In embodiments, the material is viscoelastic.

In embodiments, the optical coupler is a clear gel attached to the outer distal portion of any optical imaging or image capturing device, such as an endoscope or camera lens. When pressed in contact with the surface of an area to be viewed, the gel creates an offset that allows clear visualization by mechanically displacing the opaque liquid or soft semisolids.

The material used to form the optical coupler can be comprised of two or more compounds, for example an opaque compound attaches and holds two visualization portions of a coupler in position, the first visualization portion is an inner clear semi rigid compound shaped to match the field of view and minimum depth field of the imaging system, and the second portion is attached to the outer boundary of the first visualization portion and is composed of very soft gel providing additional area of fluid displacement for maneuvering and positioning instruments under direct vision. In embodiments, the two or more compounds each can be of materials that exhibit transparency or translucency. Methods described in U.S. Pat. Nos. 7,235,592 and 7,205,339 can be utilized to produce a coupler with portions or areas of the gel with different physical properties.

Referring back to FIGS. 1-3, in the optical coupler 10, the material is optically clear such that the light guide 39 can transmit light through the optical coupler 10 toward a surface area at or beyond the outer surface 14 of the optical coupler 10 and such that the optical coupler 10 is capable of transmitting an optical image of the surface area being viewed back to the lens 40. In embodiments, the material has a degree of light transmittance greater than 80% based on test standard ASTM D-1003 (Standard Test Method for Haze and Luminous Transmittance of Transparent Plastics). In other embodiments, the material has a degree of light transmittance greater than 98% based on test standard ASTM D-1003. In embodiments, the material has an optical absorption of less than 0.1%) in the visible light range, and, in embodiments, an optical absorption of less than 0.01%; in the visible light range. In embodiments, the material has an index of refraction of about 1.3 to about 2.2, and in embodiments, the index of refraction of the material matches the index of refraction of the light guide 39, or is as low as possible.

The optical coupler 10 may also be coated. Coating may reduce the amount of adherence properties and/or reduce unwanted light reflections, and/or change and enhance the optical coupler by adding hydrophobic or hydrophilic properties. Suitable coatings that may be used on the optical coupler include, but are not limited to, polymers based on p-xylylene, such as for example, polymers that are commercially available under the trade name Parylene C, which is an optically clear biocompatible polymer having abrasion resistant and hydrophobic or hydrophilic properties.

EXAMPLES

The following Examples have been presented in order to further illustrate the devices and methods described herein and are not intended to limit the invention(s) in any way.

Example 1

A series of optical couplers in a shape similar to that of FIG. 3 was molded from Nusil MED-6033 an optical grade liquid silicone elastomer available from Nusil Technologies, Carpinteria, California. This silicone has an index of refraction of 1.41, and a durometer of about 45 on the Shore 00 scale. The surface of the mold forming the outer surface of the optical coupler was manufactured using a micropolishing methodology to impart a surface finish better than the Society of Plastic Industry (SP1) Al finish on to the mold. The surface finish of the mold and the resulting lenses were measured using a Zygo interferometer to determine the surface finish on the distal surface of the optical coupler.

These optical couplers were then placed on a number of scopes, including an Olympus CF-Q160A/L colonoscope, a 10 mm rigid laparoscope and a Pentax EG-2990 gastroscope. The visual performance of these optical couplers was observed to determine the impact of surface finish on the visual performance of these scopes without an optical coupler and with an optical coupler. and the following was noted: The lenses measured with this approach had the following attributes:

TABLE A

| Optical Coupler | Surface Roughness (RMS) | Surface Roughness (Ra) | Interfere With Image (Yes/No) |
|---|---|---|---|
| 1 | 21.1646 nm | 10.2766 nm | Yes |
| 2 | 40.3157 nm | 18.0538 nm | Yes |
| 3 | 32.9431 nm | 13.8726 nm | Yes |
| 4 | 25.1743 nm | 11.4089 nm | Yes |
| 5 | 12.0249 nm | 8.5337 nm | No |
| 6 | 12.7432 nm | 10.1406 nm | No |

To further assess the variations in the surface finish of the optical couplers, assessments were performed by placing the couplers on the scopes mentioned above and moving various targets in close and away from the endoscope, at specific distances ranging from 3 mm out to several centimeters to assess how changes in light and object distance impact optical performance, relative to surface finish. In addition, the optical couplers were tested at these various distances in situations involving fluid and debris to determine the impact of various levels of surface finish and various distances and environments on visual performance. The performance of these optical couplers was compared to the performance of a scope without the optical coupler to determine an acceptable surface finish that did not interfere with the capture of the visual image through the optical coupler.

As can be seen from the data in Table A, a surface roughness of less than 12.7432 nm RMS did not interfere with the video capture and autofocus software, while surface roughness in excess of this level of surface roughness confused the software, and caused the image of target tissue displayed by the endoscope to be intermittently out of focus. Further, when lenses were tested on scopes without imaging software, the glare and reflection was unacceptably high, inhibiting performance, at the surface roughness greater than 12.7432 nm RMS.

Persons skilled in the art will understand that the devices and methods specifically described herein and illustrated in the accompanying drawings are non-limiting exemplary embodiments. The features illustrated or described in connection with one exemplary embodiment may be combined with the features of other embodiments. Such modifications and variations are intended to be included within the scope of the present disclosure. As well, one skilled in the art will appreciate further features and advantages of the present disclosure based on the above-described embodiments. Accordingly, the present disclosure is not to be limited by what has been particularly shown and described, except as indicated by the appended claims.

It should be understood that the foregoing description is only illustrative of the present disclosure. Various alternatives and modifications can be devised by those skilled in the art without departing from the disclosure. For example, the coupler may be used in non-medical applications wherein the coupler is attached to the distal end of a borescope or attached to micro, conventional, or robotic video cameras, inspection scopes, or still cameras, thereby allowing viewing and/or making repairs inside pipes, holding tanks, containers, etc. without the need to empty the pipes or containers of static or moving opaque fluid, such as petroleum products, sewerage, food products, paint, etc. In non-medical, industrial applications, the coupler can be formed from materials that resist acid, alkalinity, high heat, or viscosity of fluid being displaced by the coupler and may be reusable. Accordingly, the present disclosure is intended to embrace all such alternatives, modifications and variances. The embodiments described with reference to the attached drawing figures are presented only to demonstrate certain examples of the disclosure. Other elements, steps, methods and techniques that are insubstantially different from those described above and/or in the appended claims are also intended to be within the scope of the disclosure.

What is claimed is:

1. An optical coupler for mounting to a distal end of an endoscope, the coupler comprising:
    a visualization section at one end of the coupler, the visualization section including a proximal surface and an outer surface spaced apart from the proximal surface, wherein at least one of the proximal surface or the outer surface of the visualization section has an average surface roughness less than about 50 nanometers RMS; and
    an attachment section connected to and extending away from the visualization section, the attachment section being dimensioned to be mounted at the distal end of the endoscope,
    wherein the visualization section has an index of refraction of about 1.3 to about 2.2.

2. The optical coupler of claim 1, further comprising a polymer coating on the outer surface of the visualization section.

3. The optical coupler of claim 1, wherein the visualization section comprises substantially transparent material for transmitting light therethrough.

4. The optical coupler of claim 1, wherein the visualization section comprises a material selected from the group consisting of glass, silicone gels, silicone elastomers, epoxies, polyurethanes, polycarbonates, acrylics, and combinations thereof.

5. The optical coupler of claim 1, wherein at least one of the proximal surface or the outer surface of the visualization section has a plurality of depressions with an average diameter less than about 150 nanometers.

6. The optical coupler of claim 1, wherein at least one of the proximal surface or the outer surface of the visualization section has a plurality of depressions with an average diameter from about 15 to about 100 nanometers.

7. The optical coupler of claim 1, wherein at least one of the proximal surface or the outer surface of the visualization section has a plurality of depressions having an average density less than about 100 depressions per 100 square micrometers.

8. The optical coupler of claim 1, wherein at least one of the proximal surface or the outer surface of the visualization section has a plurality of depressions having an average density of from about 10 to about 50 depressions per 100 square micrometers.

9. The optical coupler of claim 1, wherein at least one of the proximal surface or the outer surface of the visualization section has an average surface roughness of from about 5 to about 30 nanometers RMS.

10. The optical coupler of claim 1, wherein at least one of the proximal surface or the outer surface of the visualization section has an average surface roughness less than about 50 nanometers RMS measured at spatial frequencies between $1 \times 10^{-1}$ mm$^{-1}$ to $1 \times 10^{3}$ mm$^{-1}$.

11. An optical coupler for mounting at a distal end of an endoscope, the coupler comprising:
- a visualization section at one end of the coupler, the visualization section including a proximal surface and an outer surface spaced apart from the proximal surface, wherein at least one of the proximal surface or the outer surface of the visualization section has an average surface roughness less than about 50 nanometers RMS;
- an attachment section connected to and extending away from the visualization section, the attachment section being dimensioned to be mounted at the distal end of the endoscope; and
- a light emitting element near, or on, the outer surface of the visualization section.

12. The optical coupler of claim 11, wherein the light emitting element comprises a light emitting diode (LED).

13. The optical coupler of claim 11, wherein the visualization section has an index of refraction of about 1.3 to about 2.2.

14. The optical coupler of claim 11, wherein the visualization section comprises a material selected from the group consisting of glass, silicone gels, silicone elastomers, epoxies, polyurethanes, polycarbonates, acrylics, and combinations thereof.

15. The optical coupler of claim 11, wherein at least one of the proximal surface or the outer surface of the visualization section has a plurality of depressions with an average diameter less than about 150 nanometers.

16. The optical coupler of claim 11, wherein at least one of the proximal surface or the outer surface of the visualization section has a plurality of depressions with an average diameter from about 15 to about 100 nanometers.

17. The optical coupler of claim 11, wherein at least one of the proximal surface or the outer surface of the visualization section has a plurality of depressions having an average density less than about 100 depressions per 100 square micrometers.

18. The optical coupler of claim 11, wherein at least one of the proximal surface or the outer surface of the visualization section has a plurality of depressions having an average density of from about 10 to about 50 depressions per 100 square micrometers.

19. The optical coupler of claim 11, wherein at least one of the proximal surface or the outer surface of the visualization section has an average surface roughness of from about 5 to about 30 nanometers RMS.

* * * * *